United States Patent [19]

Tokarski et al.

[11] Patent Number: 5,315,923
[45] Date of Patent: May 31, 1994

[54] METHOD OF PREPARING PAPERBOARD FOOD AND BEVERAGE CONTAINERS FOR RECYCLING

[75] Inventors: Michael G. Tokarski, Dublin; Lester A. Roudabush, Delaware, both of Ohio

[73] Assignee: Combibloc, Inc., Columbus, Ohio

[21] Appl. No.: 944,397

[22] Filed: Sep. 14, 1992

[51] Int. Cl.⁵ .............................. B30B 13/00
[52] U.S. Cl. ........................ 100/39; 100/35; 100/71; 100/96; 241/22
[58] Field of Search ............ 100/35, 70 R, 71, 92, 100/94–97, 39; 252/194; 241/22

[56] References Cited

U.S. PATENT DOCUMENTS

| | | | |
|---|---|---|---|
| 2,933,455 | 4/1960 | Doying | 252/194 |
| 3,315,588 | 4/1967 | Lorenz | 100/71 X |
| 3,986,845 | 10/1976 | Hotchkiss | 100/97 X |
| 4,102,263 | 7/1978 | Forsberg | 100/97 X |
| 4,270,447 | 6/1981 | Gregorovic | 100/70 R |
| 4,352,267 | 10/1982 | Mellinger | 100/71 X |
| 4,961,862 | 10/1990 | Janecek | 100/71 X |
| 5,190,725 | 3/1993 | Meijer et al. | 241/22 X |

FOREIGN PATENT DOCUMENTS 2155764  5/1973  France ................... 100/35

*Primary Examiner*—Stephen F. Gerrity
*Attorney, Agent, or Firm*—Porter, Wright, Morris & Arthur

[57] ABSTRACT

An apparatus for and method of preparing discarded food and beverage packagings for recycling. A moisture absorbent powder is added to the packagings prior to shipment to a recycling facility. The present invention may further include an apparatus for breaking open paperboard packages and then treating the open packages with a chemical additive such as baking soda to reduce microbial activity caused by leftover contents within the discarded packages. The packages may then be compressed and sent to a recycling facility.

8 Claims, 2 Drawing Sheets

METHOD OF PREPARING PAPERBOARD FOOD AND BEVERAGE CONTAINERS FOR RECYCLING

The present invention is generally related to the recycling of packaging materials and more particularly, is related to an apparatus and method for preparing paperboard food and beverage packaging for recycling after the contents have been used.

Paperboard food and beverage containers are capable of being recycled. Examples of methods of recycling such containers have included hydrapulping, composting, and secondary plastics (plastic lumber). Each of these methods requires a preprocessing step to prepare the packages for recycling. Typical preprocessing steps have included rinsing the packages with water and/or adding a sanitizing agent such as chlorine or quaternary ammonium compounds. A problem exists with rinsing or sanitizing; both methods leave the packages wet and when compacted, this moisture is trapped resulting in microbial activity, after the sanitizing agent(s) is spent (usually after several weeks of storage of collected and compressed packages). Microbial activity is undesirable because it may adversely effect the color, odor and quality of the recovered materials. A need exists to enhance the preprocessing of food and beverage packages to reduce the associated costs of recycling, make recycling of such structures easier, and to provide a system by which the preparation for recycling can be accomplished at various user sites prior to the reclaimed packages being shipped to a recycling facility.

The present invention addresses the above mentioned needs. The present invention offers a new process and apparatus for preparing packages to be recycled that are relatively inexpensive and easy to use. One embodiment of the present invention consists of an apparatus including dual or twin augers within a housing. At an entrance to the housing a collection hopper or chute may be positioned to receive discarded food and beverage containers and direct them to the housing so that the packages may come in contact with the augers. As the packages come in contact with the augers they are broken open (exposing the package interior) by the cutting action of the twin augers being in opposite rotation to each other. One auger may be set to rotate counterclockwise while the other auger rotates clockwise.

Along the path of the housing holding the augers, a chemical additive may be introduced to the food and beverage packages by way of gravity or forced introduction through air pressure or other medium. The chemical additive is preferably a moisture absorbent powder such as baking soda which acts to reduce leftover moisture in the discarded packages and thereby retard microbial activity. This reduces odors and other undesirable aspects of used packaging recovery. Once the packages have been suitably broken open by the augers an exit path may be established to a machine such as a bailer. Once in the bailer, the broken open packages may be compressed to form a relatively large bail of paperboard ready to be shipped to a recycling facility.

In a second embodiment of the present invention a moisture absorbent powder is spread over collected packages and the packages are compressed. In this embodiment the augers are not used. The powder may be introduced directly into a compacting device such as a bailer.

The above and other features and advantages of the present invention will be better understood from the drawings and the following detailed description.

DETAILED DESCRIPTION OF PREFERRED EMBODIMENT(S)

Figure 2:
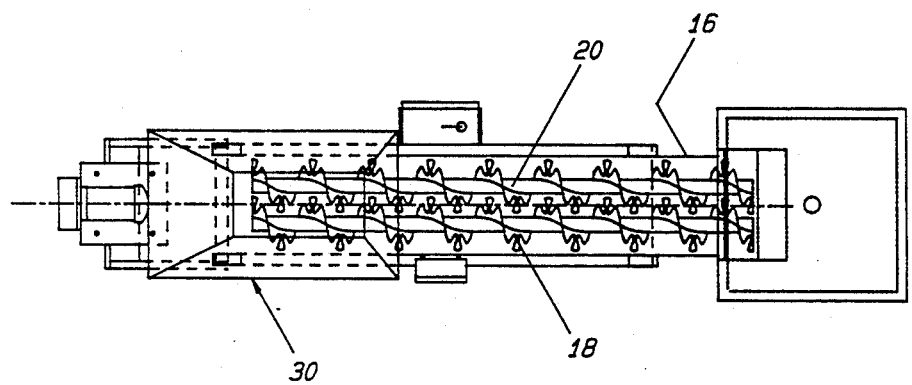
FIG. 2 is a plan view of the auger apparatus of FIG. 1.
Figure 1:
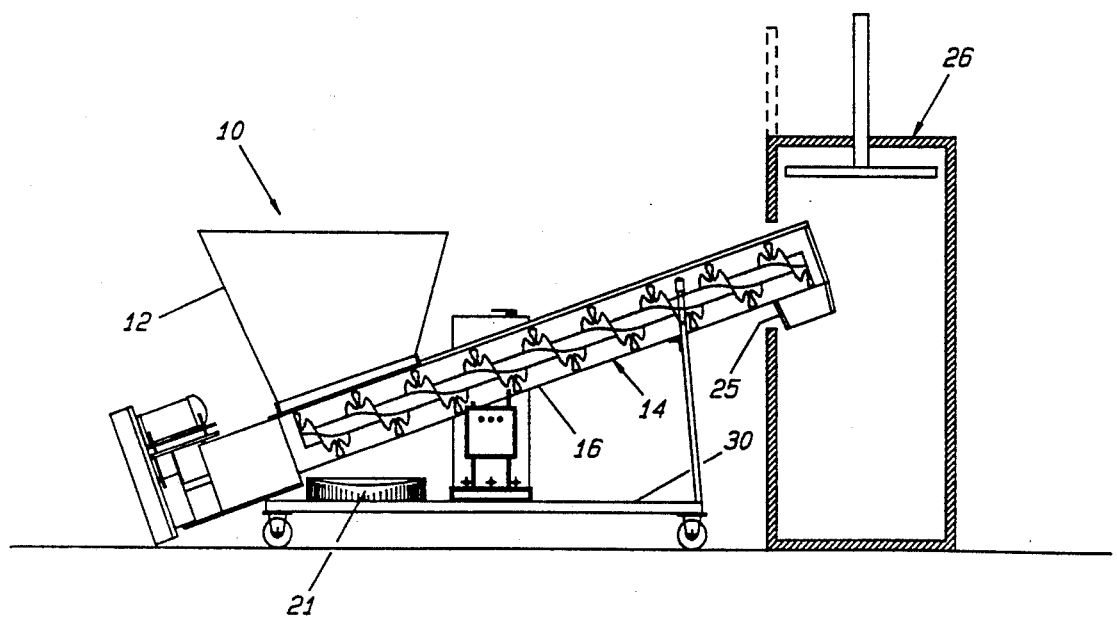
FIG. 1 is a diagram of one embodiment of the system of the present invention.
Figure 6:
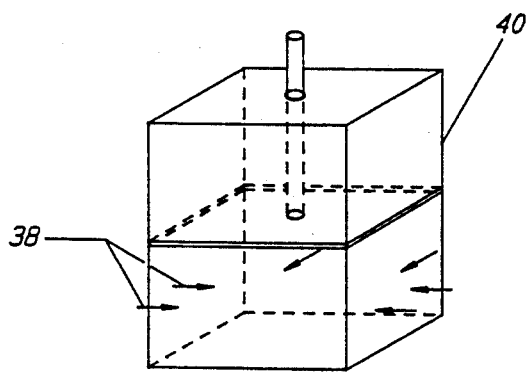
FIG. 6 is a diagrammatical representation of a bailer for use with one embodiment of the present invention.
Figure 5:
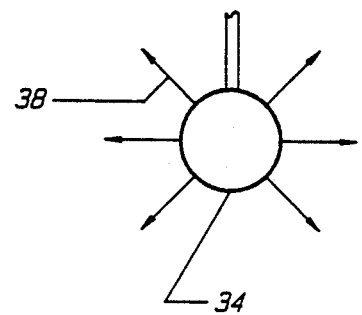
FIG. 5 is an enlarged diagrammatical representation of the control valve shown in FIG. 4.

Referring now to the drawings, and particularly FIGS. 1 and 2, there is shown a paperboard food and beverage packaging recycling preparation system 10. The system 10 includes a preferably portable packaging collection station 12 and packaging break open mechanism 14. The collection station 12 may include a hopper or chute capable of receiving a plurality of discarded food and beverage packaging structures still in their formed and shaped condition. The collection hopper or chute 12 may be designed to enable the packages to fall into a housing 16 containing packaging break open means. The manner in which the packages flow from the collection hopper or chute 12 to the break open mechanism 14 may be by gravity for example or by other means known to those of ordinary skill in the art. For example, a conveyor system may also be used to direct used packages to the break open mechanism.

Figure 3:
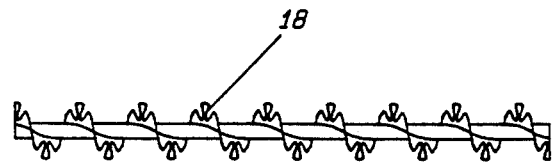
FIG. 3 is a detailed view of one preferred embodiment of an auger of the present invention.

In one embodiment of the present invention, the break open mechanism preferably is comprised of twin augers 18,20 rotating in opposite direction to each other. As the packages enter the housing 16 containing the augers 18,20, the packages come in contact with the augers and are broken open from their formed or shaped condition to an unformed condition (either flat or otherwise broken open from their "shelf shape"). The housing containing the augers is preferably inclined so that the packages remain in contact with the augers for an extended time and to facilitate draining of excess liquid from the packages. An example of an auger is shown in FIG. 3.

Along the path of the break open mechanism, the present invention may include a device 24 for the introduction of a chemical additive to the food and beverage packages. The chemical additive may be introduced by gravity means or, more preferably, by means of air pressure, thereby more evenly distributing the chemical additive over the packages. Various other means may be employed for introducing the additive, including manually introducing the additive, which would all fall under the scope of this invention. During the breaking process the augers further assist the distribution of the chemical additive. A preferred chemical additive is ordinary baking soda. Other chemical additives may be used which are moisture absorbers, including talc, corn starch or baby powder. These moisture absorbent powders are intended to greatly reduce or eliminate residual liquids remaining in the discarded food and beverage packages. By absorbing this residual moisture the chemical additive reduces odors caused by growth of microbial activity within the discarded packages.

At the exit 25 of the break open mechanism may be a bailer 26 or compactor for receiving the food and beverage packages and compressing them into a preferably rectangular shaped bail which can be readily removed and delivered to a recycling facility. The bailer or compactor may operate under any of a number of known principals of compacting materials, including the traditional piston cylinder approach, in which a plunger (rod and piston) compresses the material (discarded packages) within a cylinder (or rectangular structure). The bailer may be horizontal or vertical or may also be a different apparatus including gaylords and other compactor type storage hoppers.

In one preferred embodiment, the twin augers of the break open mechanism may be several feet long having one left hand rotating auger and one right hand rotating auger moving at 60 to 75 RPMs. The augers may each have six inch cut flights, and may be driven by a small horsepower 110 volt AC motor drive. The entire system may be mounted on a movable frame 30 that may include wheels.

The chemical additives may be stored within a holding tank 32 capable of holding many pounds of the additive in powder form. A control valve 34 may be located at the base of the holding tank 32 for controlling the flow rate of the chemical additive onto the packages. In a preferred embodiment of the present invention, an air compressor 36 is used to blow the chemical additive into the break open mechanism via a plurality of air injection lines 38 to more evenly distribute the flow of the additive onto the packages.

Figure 4:
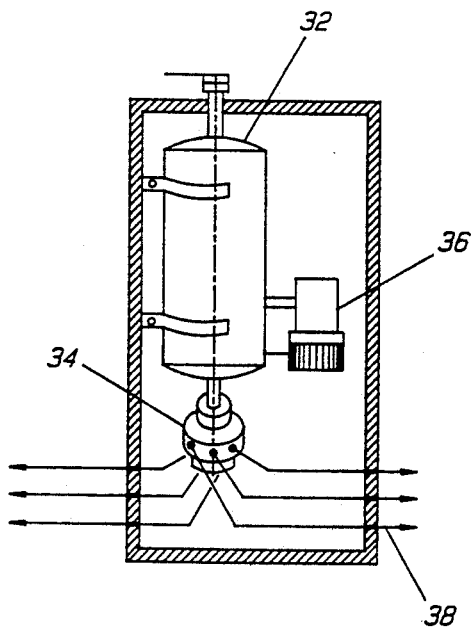
FIG. 4 is a diagram of a preferred embodiment of a chemical additive injection system of the present invention.

In a second embodiment of the present invention the break open mechanism may be eliminated. The collected packages may be introduced into a bailer 40 and the chemical additive blown into the bailer directly as shown in FIG. 4. Again, the chemical additive may be blown into the bailer through several injection lines located in different zones of the bailer. In one example, the inventor has discovered that the addition of 3 pounds of baking soda for every 100 pounds of paperboard packages has been sufficient to reduce microbial activity caused by liquid retained within the packages.

Many of the stated features and advantages of the present invention are susceptible to modification by those of ordinary skill in the art. Such modifications are an outgrowth of the invention set forth herein and thus are under the scope of this present application.

What is claimed is:

1. A method for enhancing the collection of food and beverage paperboard packaging for later recycling, said method comprising the steps of: collecting used and discarded paperboard packages, said packages having at least some moisture associated therewith; introducing said packages into a break open mechanism; adding a moisture absorbent chemical additive onto said packages while said packages are in said break open mechanism; and compressing said opened and moisture reduced packages into a bale suitable for shipment to a recycling center.

2. The method of claim 1, wherein said chemical additive is baking soda.

3. The method of claim 1, wherein said chemical additive is corn starch.

4. The method of claim 1, wherein said introduction of said chemical additive to said packages is accomplished by air pressure forcing said chemical additive onto said packages.

5. The method of claim 1, wherein said introduction of said chemical additive is accomplished by manually distributing said additive onto said packages.

6. A method for preparing packages to be recycled, said method comprising the steps of:
   collecting a plurality of discarded paperboard packagings in a collection device, said packagings having at least some moisture associated therewith;
   introducing a moisture absorbent powder onto said paperboard packagings while said packagings are in said collection device; and
   compressing said packagings after said powder has come into contact with said packagings.

7. The method of claim 6, wherein said powder is baking soda.

8. The method of claim 6, wherein said powder is corn starch.

* * * * *